United States Patent
Short

(10) Patent No.: US 6,528,249 B1
(45) Date of Patent: *Mar. 4, 2003

(54) PROTEIN ACTIVITY SCREENING OF CLONES HAVING DNA FROM UNCULTIVATED MICROORGANISMS

(75) Inventor: Jay M. Short, Encinitas, CA (US)

(73) Assignee: Diversa Corporation, San Diego, CA (US)

(*) Notice: Subject to any disclaimer, the term of this patent is extended or adjusted under 35 U.S.C. 154(b) by 180 days.

This patent is subject to a terminal disclaimer.

(21) Appl. No.: 09/713,176

(22) Filed: Nov. 14, 2000

Related U.S. Application Data

(63) Continuation of application No. 08/988,224, filed on Dec. 10, 1997, now Pat. No. 6,280,926, which is a division of application No. 08/657,409, filed on Jun. 3, 1996, now Pat. No. 5,958,672, which is a continuation-in-part of application No. 08/568,994, filed on Dec. 7, 1995, now abandoned, which is a continuation-in-part of application No. 08/503,606, filed on Jul. 18, 1995, now Pat. No. 6,004,788.

(51) Int. Cl.[7] ............................. C12Q 1/00; C12Q 1/68
(52) U.S. Cl. ................................. 435/4; 435/6
(58) Field of Search ......................... 435/4, 6

(56) References Cited

U.S. PATENT DOCUMENTS

| | | | |
|---|---|---|---|
| 5,314,935 A | 5/1994 | Arnold et al. | 435/222 |
| 5,352,778 A | 10/1994 | Comb et al. | 536/23.2 |
| 5,783,431 A | 7/1998 | Peterson et al. | 435/172.3 |
| 5,824,485 A | 10/1998 | Thompson et al. | 435/6 |

FOREIGN PATENT DOCUMENTS

| | | |
|---|---|---|
| WO | WO 91/16427 | 10/1991 |
| WO | WO 96/34112 | 10/1996 |

OTHER PUBLICATIONS

Hennecke et al., "Concurrent: evolution of nitrogenase genes and 165 rRNA in Rhizobium species and other nitrogen fixing bacteria", *Arch Microbial*, 142:342–348 (Mar. 21, 1985).

Kirshtein et al., "Amplification, Cloning, and Sequencing of a nifH Segment from Aquatic Microorganisms and Natural Communities", vol. 57, No. 9, *Applied and Environmental Microbiology*, pp. 2645–2650 (Sep. 1991).

Stein et al., "Kinetic and physical properties of a recombinant RuBisO from a chemoautotronic endosymbiont", *Molecular Marine Biology and Biotechnology*, 2(5) pp. 280–290 (1993).

Stein et al., "Nucleoside sequence and expression of a deep–sea ribulose 1,5bisphosphate carboxylase gene cloned from chemoautotrobic bacterial endosymbiont", *Proc. Natl. Acad. Sci. USA*, vol. 87 pp. 8830–8854 (Nov. 1990).

Ueda et al., "Remarkable $N_2$–Fixing Bacterial Diversity Detected in Rice Roots by Molecular Evolutionary Analysis of nifH Gene Sequences", *Journal of Bacteriology*, pp. 1414–1417 (Mar. 1995).

Zhou et al., "Random mutagenesis of gene–sized DNA molecules by use of PCR with Taq DNA polymerase", *Nucleic Acids Research*, vol. 19, No. 21, p. 6052 (Aug. 20, 1991).

*Primary Examiner*—Nashaat T. Nashed
(74) *Attorney, Agent, or Firm*—Gray Cary Ware & Freidenrich LLP; Lisa A. Haile

(57) ABSTRACT

Disclosed is a process of screening clones having DNA from an uncultivated microorganism for a specified protein, e.g. enzyme, activity by screening for a specified protein, e.g. enzyme, activity in a library of clones prepared by (i) recovering DNA from a DNA population derived from at least one uncultivated microorganism; and (ii) transforming a host with recovered DNA to produce a library of clones which is screened for the specified protein, e.g. enzyme, activity.

25 Claims, 5 Drawing Sheets

Environment Library Construction in pFOS1

1. Concentrate bacteria, digest protein and preserve high MW DNA
2. Partially digest DNA and select 40 kbp fragments by PFGE or by λ– packaging (step 3)
3. Ligate to fosmid arms, package and transfect to E. coli. Array library in microtiter plates.

PROTEIN ACTIVITY SCREENING OF CLONES HAVING DNA FROM UNCULTIVATED MICROORGANISMS

This application is a continuation of application Ser. No. 08/988,224, filed Dec. 10, 1997, now U.S. Pat. No. 6,280,926, which is a divisional application of U.S. patent application Ser. No. 08/657,409, filed on Jun. 3, 1996, now U.S. Pat. No. 5,958,672, which was a continuation-in-part of U.S. application Ser. No. 08/568,994, filed on Dec. 7, 1995, now abandoned, continuation-in-part of U.S. application Ser. No. 08/503,606, filed on Jul. 18, 1995, now U.S. Pat. No. 6,004,788.

FIELD OF THE INVENTION

This invention relates to the field of preparing and screening libraries of clones containing microbially derived DNA.

BACKGROUND OF THE INVENTION

Naturally occurring assemblages of microorganisms often encompass a bewildering array of physiological and metabolic diversity. In fact, it has been estimated that to date less than one percent of the world's organisms have been cultured. It has been suggested that a large fraction of this diversity thus far has been unrecognized due to difficulties in enriching and isolating microorganisms in pure culture. Therefore, it has been difficult or impossible to identify or isolate valuable proteins, e.g. enzymes, from these samples. These limitations suggest the need for alternative approaches to characterize the physiological and metabolic potential, i e. activities of interest of as-yet uncultivated microorganisms, which to date have been characterized solely by analyses of PCR amplified rRNA gene fragments, clonally recovered from mixed assemblage nuleic acids.

SUMMARY OF THE INVENTION

In one aspect, the invention provides a process of screening clones having DNA from an uncultivated microorganism for a specified protein, e.g. enzyme, activity which process comprises:

screening for a specified protein, e.g enzyme, activity in a library of clones prepared by
  (i) recovering DNA from a DNA population derived from at least one uncultivated microorganism; and
  (ii) transforming a host with recovered DNA to produce a library of clones which are screened for the specified protein, e.g. enzyme, activity.

The library is produced from DNA which is recovered without culturing of an organism, particularly where the DNA is recovered from an environmental sample containing microorganisms which are not or cannot be cultured.

In a preferred embodiment DNA is ligated into a vector, particularly wherein the vector further comprises expression regulatory sequences which can control and regulate the production of a detectable proteins, e.g. enzyme, activity from the ligated DNA.

The f-factor (or fertility factor) in *E. coli* is a plasmid which effects high frequency transfer of itself during conjugation and less frequent transfer of the bacterial chromosome itself. To achieve and stably propogate large DNA fragments from mixed microbial samples, a particularly preferred embodiment is to use a cloning vector containing an f-factor origin of replication to generate genomic libraries that can be replicated with a high degree of fidelity. When integrated with DNA from a mixed uncultured environmental sample, this makes it possible to achieve large genomic fragments in the form of a stable "environmental DNA library."

In another preferred embodiment, double stranded DNA obtained from the uncultivated DNA population is selected by:

converting the double stranded genomic DNA into single stranded DNA;

recovering from the converted single stranded DNA single stranded DNA which specifically binds, such as by hybridization, to a probe DNA sequence; and converting recovered single stranded DNA to double stranded DNA.

The probe may be directly or indirectly bound to a solid phase by which it is separated from single stranded DNA which is not hybridized or otherwise specifically bound to the probe.

The process can also include releasing single stranded DNA from said probe after recovering said hybridized or otherwise bound single stranded DNA and amplifying the single stranded DNA so released prior to converting it to double stranded DNA.

The invention also provides a process of screening clones having DNA from an uncultivated microorganisms for a specified protein, e.g. en~yme, activity which comprises screening for a specified gene cluster protein product activity in the library of clones prepared by: (i) recovering DNA from a DNA population derived from at least one uncultivated microorganism; and (ii3 transforming a host with recovered DNA to produce a library of clones with the screens for the specified protein, e.g enzyme, activity. The library is produced from gene cluster DNA which is recovered without culturing of an organism, particularly where the DNA gene clusters are recovered from an envirorunental sample containing microorganisms which are not or cannot be cultured.

Alternatively, double-stranded gene cluster DNA obtained from the uncultivated DNA population is selected by converting the double-stranded genomic gene cluster DNA into single-stranded DNA; recovering from the converted single-stranded gene cluster polycistron DNA, single-stranded DNA which specifically binds, such as by hybridization, to a polynucleotide probe sequence; and converting recovered single-stranded gene cluster DNA to double-stranded DNA.

These and other aspects of the present invention are described with respect to particular preferred embodiments and will be apparent to those skilled in the art from the teachings herein.

BRIEF DESCRIPTION OF THE DRAWINGS

In FIG. 1, the various classes of Tier 3 are followed by a parenthetical code which identifies the substrates of Table 1 which are used in identifying such specificities of Tier 3.

In FIGS. 2 and 3, the various classes of Tier 3 are followed by a parenthetical cede which identifies the substrates of Tables 3 and 4 which are used in identifying such specificities of Tier 3. In FIGS. 2 and 3, R2 represents the alcohol portion of the ester and R1 represents the acid portion of the ester.

FIG. 3 shows an illustration of a recombinant clone from the library which has been characterized in Tier 1 as hydrolase and in Tier 2 as ester may then be tested in Tier 3 for various specificities. In FIGS. 2 and 3, the various classes of Tier 3 are followed by a parenthetical code which identifies the substrates of Tables 3 and 4 which are used in identifying such specificities of Tier 3. In FIGS. 2 and 3, R2 represents the alcohol portion of the ester and R1 represents the acid portion of the ester.

In FIG. 4, the various classes of Tier 3 are followed by a parenthetical code which identifies the substrates of Table 5 which are used in identifying such specificities of Tier 3.

DETAIL DESCRIPTION OF THE INVENTION

Figure 1:
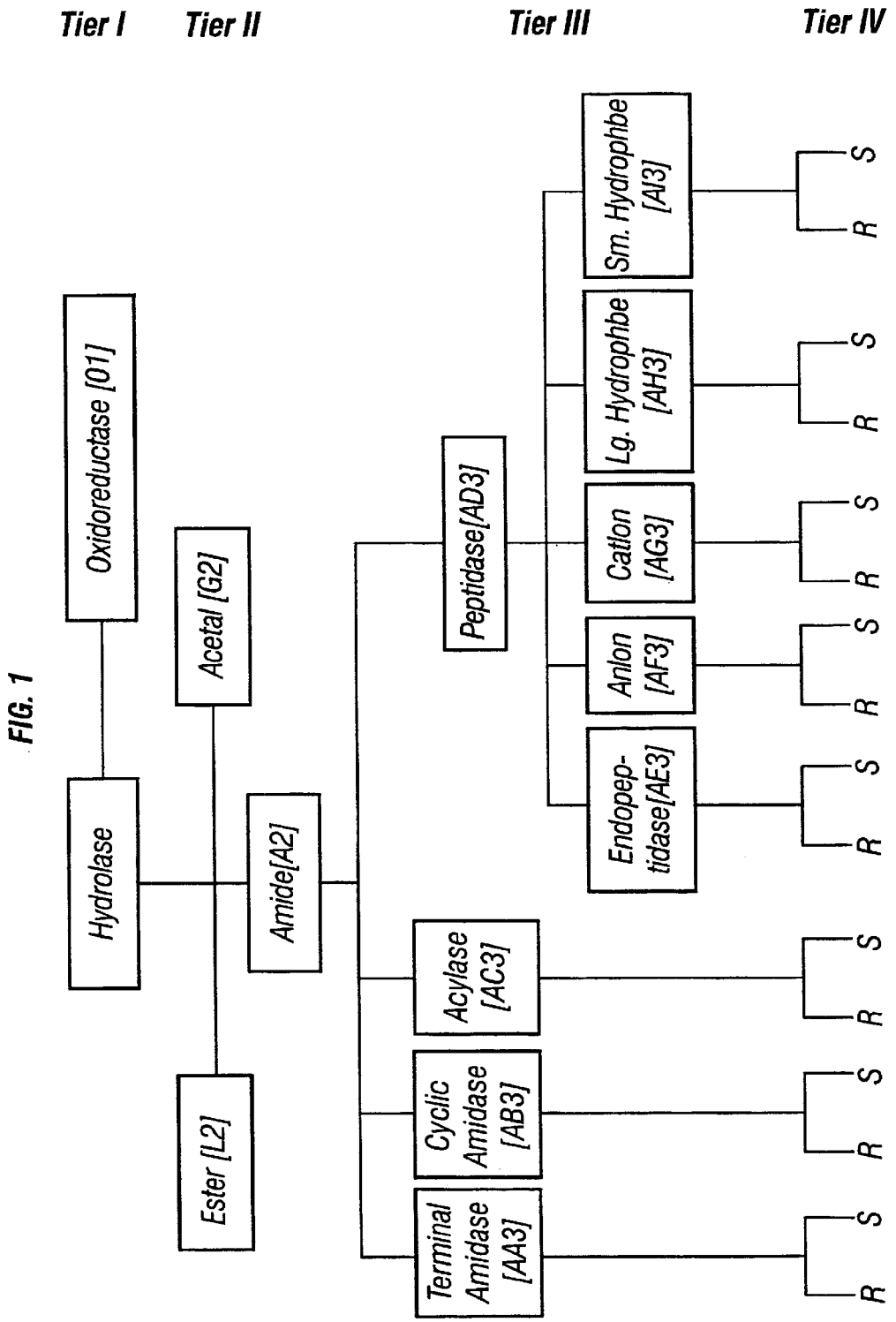
FIG. 1 shows an illustration of the Tier system for enzymes. For example, a recombinant clone from the library which has been characterized in Tier 1 as hydrolase and in Tier 2 as amide may then be tested in Tier 3 for various specificities.

The microorganisms from which the libraries may be prepared include prokaryotic microorganisms, such as Eubacteria and Archaebacteria, and lower eukaryotic microorganisms such as fungi, some algae and protozoa. The microorganisms are uncultured microorganisms obtained from environmental samples and such microorganisms may be extremophiles, such as thermophiles, hyperthermophiles, psychrophiles, psychrotrophs, etc.

As indicated above, the library is produced from DNA which is recovered without culturing of an organism, particularly where the DNA is recovered from an environmental sample containing microorganisms which are not or cannot be cultured. Sources of microorganism DNA as a starting material library from which DNA is obtained are particularly contemplated to include environmental samples, such as microbial samples obtained from Arctic and Antarctic ice, water or permafrost sources, materials of volcanic origin, materials from soil or plant sources in tropical areas. etc. Thus, for example, genomic DNA may be recovered from either uncultured or non-culturable organism and employed to produce an appropriate library of clones for subsequent determination of protein, e.g enzyme, activity.

Bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. The gene cluster, the promoter, and additional sequences that function in regulation altogether are referred to as an "operon" and can include up to 20 or more genes, usually from 2 to 6 genes. Thus, a gene cluster is a group of adjacent genes that are either identical or related, usually as to their function.

Some gene families consist of identical members. Clustering is a prerequisite for maintaining identity between genes, although clustered genes are not necessarily identical. Gene clusters range from extremes where a duplication is generated to adjacent related genes to cases where hundreds of identical genes lie in a tandem array. Sometimes no significance is discernable in a repetition of a particular gene. A principal example of this is the expressed duplicate insulin genes in some species, whereas a single insulin gene is adequate in other marunalian species.

It is important to further research gene clusters and the extent to which the full length of the cluster is necessary for the expression of the proteins resulting therefrom. Further, gene clusters undergo continual reorganization and, thus, the ability to create heterogeneous libraries of gene clusters from, for example, bacterial or other prokaryote sources is valuable in determining sources of novel proteins, particularly including proteins, e.g. enzymes, such as, for example, the polyketide syntheses that are responsible for the synthesis of polyketides having a vast array of useful activities. Other types of proteins that are the product(s) of gene clusters are also contemplated, including, for example, antibiotics, antivirals, antitumor agents and regulatory proteins, such as insulin.

Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide syntheses) are valuable as therapeutic agents. Polyketide syntheses are multifunctional proteins, e.g. enzymes, that catalyze the biosynthesis of a hugh variety of carbon chains differing in length and patterns of functionality and cyclization. Polyketide synthase genes fall into gene clusters and at least one type (designated type I) of polyketide syntheses have large size genes and proteins, e.g. enzymes, complicating genetic manipulation and in v"ro studies of these genes/proteins.

The ability to select and combine desired components from a library of polyketides and postpolyketide biosynthesis genes for generation of novel polyketides for study is appealing. The method(s) of the present invention make it possible to and facilitate the cloning of novel polyketide syntheses, since one can generate gene banks with clones containing large inserts (especially when using the f-factor based vectors), which facilitates cloning of gene clusters.

Preferably, the gene cluster DNA is ligated into a vector, particularly wherein a vector further comprises expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affect highfrequency transfer of itself during conjugation and is ideal to achieve and stably propagate large DNA fragments, such as gene clusters frorr. mixed microbial samples.

The term "derived" or "isolated" means that material is removed from its original environment (e.g., the natural environment if it is naturally occurring). For example, a naturally-occurring polynucleotide or polypeptide present in a living animal is not isolated, but the same polynucleotide or polypeptide separated from some or all of the coexisting materials in the natural system, is isolated.

The DNA isolated or derived from these microorganisms can preferably be inserted into a vector prior to probing for selected DNA. Such vectors are preferably those containing expression regulatory sequences, including promoters, enhancers and the like. Such polynucleotides can be part of a vector and/or a composition and still be isolated, in that such vector or composition is not part of its natural environment. Particularly preferred phage or plasmid and methods for introduction and packaging into them are described in detail in the protocol set forth herein.

The following outlines a general procedure for producing libraries from nonculturable organisms, which libraries can be probed to select therefrom DNA sequences which hybridize to specified probe DNA:

Obtain Biomass
DNA Isolation
Shear DNA (25 gauge needle)
Blunt DNA (Mung Bean Nuclease)
Methylate (EcoR I Methylase)
Ligate to EcoR I linkers (GGAATTCC)
Cut back linkers (EcoR I Restriction Endonuclease)
Size Fractionate (Sucrose Gradient)
Ligate to lambda vector (Lambda ZAP® (Stratagene) and gtl 1)
Package (in vitro lambda packaging extract)
Plate on *E. coli* host and amplify The probe DNA used for selectively recovering DNA of interest from the DNA derived from the at least one uncultured microorganism can be a full-length coding region sequence or a partial coding region sequence of DNA for an protein, e.g. enzyme, of known activity, a phylogenetic marker or other identified DNA sequence. The original DNA library can be preferably probed using mixtures of probes comprising at least a portion of the DNA sequence encoding the specified activity. These probes or probe libraries are preferably single-stranded and the microbial DNA which is probed has preferably been converted into single-stranded form. The probes that are particularly suitable are those derived from DNA encoding proteins, e.g. enzymes, having an activity similar or identical to the specified protein, e.g enzyme, activity which is to be screened.

The probe DNA should be at least about 10 bases and preferably at least 15 bases. In one embodiment, the entire coding region may be employed as a probe. Conditions for the hybridization in which DNA is selectively isolated by the use of at least one DNA probe will be designed to provide a hybridization stringency of at least about 50% sequence identity, more particularly a stringency providing for a sequence identity of at least about 70%.

Hybridization techniques for probing a microbial DNA library to isolate DNA of potential interest are well known in the art and any of those which are described in the literature are suitable for use herein, particularly those which use a solid phasebound, directly or indirectly bound, probe DNA for ease in separation from the remainder of the DNA derived from the microorganisms.

Preferably the probe DNA is "labeled" with one partner of a specific binding pair (i.e. a ligand) and the other partner of the pair is bound to a solid matrix to provide ease of separation of target from its source. The ligand and specific binding partner can be selected from, in either orientation, the following: (1) an antigen or hapten and an antibody or specific binding fragment thereof; (2) biotin or iminobiotin and avidin or streptavidin; (3) a sugar and a lectin specific therefor; (4) a protein, e.g. enzyme, and an inhibitor therefor; (5) an apoenzyrne and cofactor; (6) complementary homopolymeric oligonucleotides; and (7) a hormone and a receptor therefor. The solid phase is preferably selected from: (1) a glass or polymeric surface; (2) a packed column of polymeric beads: and (3) magnetic or paramagnetic particles.

The library of clones prepared as described above can be screened directly for enzymatic activity without the need for culture expansion, amplification or other supplementary procedures. However, in one preferred embodiment, it is considered desirable to amplify the DNA recovered from the individual clones such as by PCR.

Further, it is optional but desirable to perform an amplification of the target DNA that has been isolated. In this embodiment the selectively isolated DNA is separated from the probe DNA after isolation. It is then amplified before being used to transform hosts. The double stranded DNA selected to include as at least a portion thereof a predetermined DNA sequence can be rendered single stranded, subjected to amplification and reannealed to provide amplified numbers of selected double stranded DNA. Numerous amplification methodologies are now well known in the art.

The selected DNA is then used for preparing a library for screening by transforming a suitable organism. Hosts, particularly those specifically identified herein as preferred, are transformed by artificial introduction of the vectors containing the target DNA by inoculation under conditions conducive for such transformation.

The resultant libraries of transformed clones are then screened for clones which display activity for the protein, e.g. enzyme, of interest in a phenotypic assay for protein, e.g. enzyme, activity.

Having prepared a multiplicity of clones from DNA selectively isolated from an organism, such clones are screened for a specific protein, e.g. enzyme, activity and to identify the clones having the specified protein, e.g enzyme, characteristics.

The screening for protein, e.g. enzyme, activity may be effected on individual expression clones or may be initially effected on a mixture of expression clones to ascertain whether or not the mixture has one or more specified protein, e.g. enzyme, activities. If the mixture has a specified protein. e.g. eryme, activity, then the individual clones may be rescreened for such protein, e.g. enzyme, activity or for a more specific activity. Thus, for example, if a clone mixture has hydrolase activity, then the individual clones may be recovered and screened to determine which of such clones has hydrolase activity.

The DNA derived from a microorganism(s) is preferably inserted into an appropriate vector (generally a vector containing suitable regulatory sequences for effecting expression) prior to subjecting such DNA to a selection procedure to select and isolate therefrom DNA which hybridizes to DNA derived from DNA encoding an proteins, e.g. enzyme(s), having the specified protein, e.g. enzyme, activity.

As representative examples of expression vectors which may be used there may be mentioned viral particles, baculovirus, phage, plasmids, phagemids, cosmids, phosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus, yeast, etc.) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE70, pQE60, pQE-9 (Qiagen), pBLUESCRIPT SK, pBLUESCRIPT KS (Stratagene); pTRC99a, pKK223-3, pDR540, pRIT2T (Pharmacia); Eukaryotic: pWLNEO, pXTI, pSG5 (Stratagene) pSVK3, pBPV, pMSG, pSV-LSV40 (Pharmacia). However, any other plasmid or vector may be used as long as they are replicable and viable in the host.

A particularly preferred type of vector for use in the present invention contains an f-factor origin of replication. The f-factor (or fertility factor) in E. coli is a plasmid which effects high frequency transfer of itself during conjugation and less frequent transfer of the bacterial chromosome itself. A particularly preferred embodiment is to use cloning, vectors, referred to as "fosmids" or bacterial artificial chromosome (BAC) vectors. These are derived from the E. coli f-factor and are able to stably integrate large segments of genomic DNA. When integrated with DNA from a mixed uncultured environmental sample, this makes it possible to achieve large genomic fragments in the form of a stable "environmental DNA library."

The DNA derived from a microorganism(s) may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. Particular named bacterial promoters include lacI, lacZ, T3, T7, apt, lambda PR, PL and trp. Eukaryotic promoters include CMV immediate early, HSV thymidine kinase, early and late SV40. LTRs from retrovirus, and mouse metallotnionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Generally, recombinant expression vectors will include origins of replication and selectable markers permitting transformation of the host cell, e.g, the ampicillin resistance gene of E. coli and S. cerevisiae TRP1 gene, and a promoter derived from a highly-expressed gene to direct transcription of a downstream structural sequence. Such promoters can be derived from operons encoding glycolytic proteins, e.g enzymes, such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The DNA selected and isolated as hereinabove described is introduced into a suitable host to prepare a library which is screened for the desired protein, e.g. enzyme, activity. The selected DNA is preferably already in a vector which includes appropriate control sequences whereby selected DNA which encodes for an protein, e.g enzyme, may be expressed, for detection of the desired activity. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by transformation, calcium phosphate transfection, DEAE-Dextran mediated transfection, DMSO or electroporation (Davis, L., Dibner, M., Battey, I., Basic Methods in Molecular Biology, (1986)).

As representative examples of appropriate hosts, there may be mentioned: bacterial cells, such as E. coli, Bacillus, Streptomyces, *Salmonella typhimurium*; fungal cells, such as yeast; insect cells such as Drosophila S2 and Spodoptera SJ9; animal cells such as CHO, COS or Bowes melanoma; adenoviruses; plant cells, etc.

The selection of an appropriate host is deemed to be within the scope of those skilled in the art from the teachings herein.

Host cells are genetically engineered (transduced or transformed or transfected) w~th the vectors. The engineered host cells can be cultured in conventional nutrient media modified as appropriate for activating promoters, selecting transfonnants or amplifying genes. The culture conditions, such as temperature, pH and the like, are those previously used with the host cell selected for expression, and will be apparent to the ordinarily skilled artisan.

The library may be screened for a specified protein, e.g. enzyme, activity by procedures known in the art. For example, the protein, e.g enzyme, activity may be screened for one or more of the six IUB classes; oxidoreductases, transferases, hydrolases, lyases, isomerases and ligases. The recombinant proteins, e.g. enzymes, which are determined to be positive for one or more of the IUB classes may then be rescreened for a more specific protein, e.g. enzyme, activity.

Alternatively, the library may be screened for a more specialized protein, e.g enzyme, activity. For example, instead of generically screening for hydrolase activity, the library may be screened for a more specialized activity, i.e. the type of bond on which the hydrolase acts. Thus, for example, the library may be screened to ascertain those hydrolases which act on one or more specified chemical functionalities, such as: (a) amide (peptide bonds), i.e. proteases; (b) ester bonds, i.e. esterases and lipases; (c) acetals, i.e, glycosidases etc.

The clones which are identified as having the specified protein, e g. enzyme, activity may then be sequenced to identify the DNA sequence encoding an protein, e.g. enzyme, having the specified activity. Thus, in accordance with the present invention it is possible to isolate and identify: (i) DNA encoding an protein, e.g enzyme, having a specified protein, e.g. enzyme, activity, (ii) proteins, e.g. enzymes, having such activity (inlcuding the amino acid sequence thereof) and (iii) produce recombinant proteins, e.g. enzymes, having such activity.

The present invention may be employed for example, to identify uncultured microorganisms with proteins, e.g. enzymes, having, for example, the following activities which may be employed for the following uses:

1. Lipase/Esterase
    a. Enantioselective hydrolysis of esters (lipids)/thioesters
        1) Resolution of racemic mixtures
        2) Synthesis of optically active acids or alcohols from mesodiesters
    b. Selective syntheses
        1) Regiospecific hydrolysis of carbohydrate esters
        2) Selective hydrolysis of cyclic secondary alcohols
    c. Synthesis of optically active esters, lactones, acids, alcohols
        1) Transesterification of activated/nonactivated esters
        2) Interesterification
        3) Optically active lactones from hydroxyesters
        4) Regio- and enantioselective ring opening of anhydrides
    d. Detergents
    e. Fat/Oil conversion
    f. Cheese ripening
2. Protease
    a. Ester/amide synthesis
    b. Peptide synthesis
    c. Resolution of racemic mixtures of amino acid esters
    d. Synthesis of non-natural amino acids
    e. Detergents/protein hydrolysis
3. Glycosidase/Glycosyl transferase
    a. Sugar/polymer synthesis
    b. Cleavage of glycosidic linkages to form mono, all-and oligosaccharides
    c. Synthesis of complex oligosaccharides
    d. Glycoside synthesis using UDP-galactosyl transferase
    e. Transglycosylation of disaccharides, glycosyl fluorides, aryl galactosides
    f. Glycosyl transfer in oligosaccharide synthesis
    g. Diastereoselective cleavage of p-glucosylsulfoxides
    h. Asymmetric glycosylations
    i. Food processing
    j. Paper processing
4. Phosphatase/Kinase
    a. Synthesis/hydrolysis of phosphate esters
        1) Regio-, enantioselective phosphorylation
        2) Introduction of phosphate esters
        3) Synthesize phospholipid precursors
        4) Controlled polynucleotide synthesis
    b. Activate biological molecule
    c. Selective phosphate bond formation without protecting groups
5. Mono/Dioxygenase
    a. Direct oxyfunctionalization of unactivated organic substrates
    b. Hydroxylation of alkane, aromatics, steroids
    c. Epoxidation of alkenes
    d. Enantioselective sulphoxidation
    e. Regio- and stereoselective Bayer-Villiger oxidation
6. Haloperoxidase
    a. Oxidative addition of halide ion to nucleophilic sites
    b. Addition of hypohalous acids to olefinic bonds
    c. Ring cleavage of cyclopropanes
    d. Activated aromatic substrates converted to ortho and para derivatives
    e. 1.3 diketones converted to 2-halo-derivatives
    f. Heteroatom oxidation of sulfur and nitrogen containing substrates
    g. Oxidation of enol acetates, alkynes and activated aromatic rings
7. Lignin peroxidase/Diarylpropane peroxidase
    a. Oxidative cleavage of C—C bonds
    b. Oxidation of benzylic alcohols to aldehydes
    c. Hydroxylation of benzylic carbons
    d. Phenol dimerization
    e. Hydroxylation of double bonds to form diols
    f. Cleavage of lignin aldehydes
8. Epoxide hydrolase
    a. Synthesis of enantiomerically pure bioactive compounds
    b. Regio- and enantioselective hydrolysis of epoxide Aromatic and olefinic epaxidation by monoaxygenases to form epoxides
    d. Resolution of racemic epoxides
    e. Hydrolysis of steroid epoxides
9. Nitrile hydratase/nitriluse
    a. Hydrolysis of aliphatic nitriles to carboxamides
    b. Hydrolysis of aromatic, heterocyclic, unsaturated aliphatic nitriles to corresponding acids
    c. Hydrolysis of acrylonitrile
    d. Production of aromatic and carboxamides, carboxylic acids (nicotinamide, picolinamide, isonicotinamide)
    e. Regioselective hydrolysis of acrylic dinitrile
    f. α-amino acids from a-hydroxynitriles
10. Transaminase
    a. Transfer of amino groups into oxo-acids
11. Amidase/Acylase
    a. Hydrolysis of amides, arnidines, and other C—N bonds
    b. Non-natural amino acid resolution and synthesis Preparatlon of a Representative DNA Library The following outlines the procedures used to generate a gene library from a sample of the exterior surface of a whale bone found at 1240 meters depth in the Santa Catalina Basin during a dive expedition.

Isolate DNA

ISOQUICK Procedure as per manufacturer's instructions.

Shear DNA

1. Vigorously push and pull DNA through a 25G double-hub needle and 1-cc syringes about 500 times.
2. Check a small amount (0.5 μg) on a 0.8% agarose gel to make sure the majority of the DNA is in the desired size range (about 3–6 kb).

Blunt DNA

1. Add:
   $H_2O$ to a final volume of 405 μl
   45 μl 10×Mung,Bean Buffer 2.0 μl Mung Bean Nuclease (150 μ/μl)
2. Incubate 37° C., 15 minutes.
3. Phenol/chloroform extract once.
4. Chloroform extract once.
5. Add 1 ml ice coli ethanol to precipitate.
6. Place on ice for 10 minutes.
7. Spin in microfuge, high speed, 30 minutes.
8. Wash with 1 ml 70% ethanol.
9. Spin in microfuge, high speed, 10 minutes and dry. to a final volume of 4.0 μl Methylate DNA 1. Gently resuspend DNA in 26 μl TE.
2. Add:
   4.0 μl 10×EcoR I Methylase Buffer
   0.5 μl SAM (32 mM)
   5.0 μl EcoR I Methylase (40 μ/μl)
3. Incubate 37°, 1 hour Insure Blunt Ends 1. Add to the methylation reaction:
   5.0 μl 100 mM $MgCl_2$
   8.0 μl dNTP mix (2.5 mM of each dGTP, dATP, dTTP, dCTP) 4.0 μl Klenow (5 μ/μl)
2. Incubate 12° C., 30 minutes.
3. Add 450 μl 1×STE.
4. Phenol/chloroform extract once.
5. Chloroform extract once.
6. Add 1 ml ice coli ethanol to precipitate and place on ice for 10 minutes.
7. Spin in microfuge, high speed, 30 minutes.
8. Wash with 1 ml 70% ethanol.
9. Spin in microfuge, high speed, 10 minutes and dry.

Linker Ligation

1. Gently resuspend DNA in 7 μl Tris-EDTA (TE).
2. Add:
   14 μl Phosohorvlated EcoR I linkers (200 ng,/μl)
   3.0 μl 10×Ligation Buffer
   3.0 μl 10 mM rATP
   3.0 μl T4 DNA Ligase (4 Wu/μl)
3. Incubate 4° C., overnight.

EcoRI Cutback

1. Heat kill ligation reaction 68° C., 10 minutes.
2. Add:
   237.9 $H_2O$
   30 μl 10×EcoR I Buffer
   2.1 μl EcoR I Restriction Enzyme (100 u/μl)
3. Incubate 37° C., 1.5 hours.

4. Add 1.5 μl 0.5 M EDTA.
5. Place on ice.

Sucrose Gradient (2.2 ml) Size Fractionation

1. Heat sample to 65° C., 10 minutes.
2. Gently load on 2.2 ml sucrose gradient.
3. Spin in mini-ultracentriflge, 45K, 20° C., 4 hours (no brake).
4. Collect fractions by puncturing the bottom of the gradient tube with a 20 G needle and allowing the sucrose to flow through the needle. Collect the first 20 drops in a Falcon 2059 tube then collect 10 1-drop fractions (labelled 1–10). Each drop is about 60 μl in volume.
5. Run 5 μl of each fraction on a 0.8% agarose gel to check the size.
6. Pool fractions 1–4 (–10–1.5 kb) and, in a separate tube, pool fractions 5–7 (about 5–0.5 kb).
7. Add 1 ml ice coli ethanol to precipitate and place on ice for 10 minutes.
8. Spin in microfuge, high speed, 30 minutes.
9. Wash with 1 ml 70% ethanol.
10. Spin in microfuge, high speed, 10 minutes and dry.
11. Resuspend each in 10 μl TE buffer.

Test Ligation to Lambda Arms

1. Plate assay to get an approximate concentration. Spot 0.5 μl of the sample on agarose containing ethidium bromide along with standards (DNA samples of known concentration). View in UV light and estimate concentration compared to the standards. Fraction 1–4=>1.0 μg/μl 1. Fraction 5–7=500 ng/μl.
2. Prepare the following ligation reactions (5 μl reactions) and incubate 4° C., overnight:

| Sample | $H_2O$ | 10 × Ligase Buffer | 10 mM rATP | Lambda arms (gt11 and ZAP) | Insert DNA | T4 DNA Ligase (4 Wu/μ) |
|---|---|---|---|---|---|---|
| Fraction 1–4 | 0.5 μl | 0.5 μl | 0.5 μl | 1.0 μl | 2.0 μl | 0.5 μl |
| Fraction 5–7 | 0.5 μl | 0.5 μl | 0.5 μl | 1.0 μl | 2.0 μl | 0.5 μl |

Test Package and Plate

1. Package the ligation reactions following manufacturer's protocol. Package 2.5 μl per packaging extract (2 extracts per ligation).
2. Stop packaging reactions with 500 μl SM buffer and pool packaging that came from the same ligation.
3. Titer 1.0 μl of each on appropriate host (OD6W=1.0) [XLIBlue MRF for ZAP® (Stratagene) and Y1088 for gtl 1]
   Add 200 μl host (in mM $MgSO_4$) to Falcon 2059 tubes
   Inoculate with 1 μl packaged phage
   Incubate 37° C., 15 minutes
   Add about 3 ml 48° C. top agar [50 ml stock containing 150 μl IPTG (0.5M) and 300 μl X-GAL (350 mg/ml)]
   Plate on 100 mm plates and incubate 37° C., overnight.
4. Efficiency Results:
   gtl1: $1.7 \times 10^4$ recombinants with 95% background
   ZAP® (Stratagene): $4.2 \times 10^4$ recombinants with 66% background Contaminants in the DNA sample may have inhibited the enzymatic reactions, though the sucrose gradient and organic extractions may have removed them. Since the DNA sample was precious, an effort was made to "fix" the ends for cloning:

Re-Blunt DNA

1. Pool all left over DNA that was not ligated to the lambda arms (Fractions 1–7) and add H$_2$O to a final volume of 12 µl. Then add:
   143 µl H$_2$O
   20 µl 10×Buffer 2 (from Stratagene's cDNA Synthesis Kit)
   23 µl Blunting dNTP (from Stratagene's cDNA Synthesis Kit)
   2.0 µl Pfu (from Stratagene"s cDNA Synthesis
2. Incubate 72° C., 30 minutes.
3. Phenol/chloroform extract once.
4. Chloroform extract once.
5. Add 20 µL 3M NaOAc and 400 µl ice coli ethanol to precipitate.
6. Place at −20° C., overnight.
7. Spin in microfuge, high speed, 30 minutes.
8. Wash with 1 ml 70% ethanol.
9. Spin in microfuge, high speed, 10 minutes and dry.

(Do NOT Methylate DNA since it was already methylated in the first round of processing)

Adaptor Ligation

1. Gently resuspend DNA in 8 Ill EcoR I adaptors (from Stratagene's cDNA Synthesis Kit).
2. Add:
   1.0 µl 10×Ligation Buffer
   10 µl 10 mM rATP
   1.0 µl T4 DNA Ligase (4 Wu/µl)
3. Incubate 4° C., 2 days.

(Do NOT cutback since using ADAPTORS this time. Instead, need to phosphorylate)

Phosphorylate Adaptors

1. Heat kill ligation reaction 70° C., 30 minutes. Add:
   1.0 µl 10×Ligation Buffer
   2.0 µl 10 mM rATF
   6.0 µl H$_2$O
   1.0 µl PNK (from Stratagene's cDNA Synthesis Kit).
2. Incubate 37° C., 30 minutes.
3. Add 31 µl H$_2$O and 5 µl 10×STE.
4. Size fractionate on a Sephacryl S-500 spin column (pool fractuions 1–3).
5. Phenol/chloroform extract once.
6. Chloroform extract once.
7. Add ice coli ethanol to precipitate.
8. Place on ice, I0 minutes.
9. Spin in microfuge, high speed, 30 minutes.
10. Wash with 1 ml 70% ethanol.
11. Spin in microfuge, high speed, 10 minutes and dry.
12. Resuspend in 10.5 µl TE buffer.

Do not plate assay. Instead, ligate directly to arms as above escept use 2.5 µl of DNA and no water.

Package and Titer as Above.

Efficiency results:
   gtl1: 2.5×10$^6$ recombinants with 2.5% background
   ZAP® (Stratagene): 9.6×10$^5$ recombinants with 0% background Amplification of Libraries (5.0×10$^5$ Recombinants from Each Library)

1. Add 3.0 ml host cells (OD$_{660}$=1.0) to two 50 ml conical tube.
2. Inoculate with 2.5×10$^5$ pfu per conical tube.
3. Incubate 37° C., 20 minutes.
4. Add top agar to each tube to a final volume of 45 ml.
5. Plate the tube across five 150 mm plates.
6. Incubate 37° C., 6–8 hours or until plaques are about pin-head in size.
7. Overlay with 8–10 ml SM Buffer and place at 4° C. overnight (with gentle rocking if possible).

Harvest Phage

1. Recover phage suspension by pouring the SM buffer off each plate into a 50-ml conical tube.
2. Add 3 ml chloroform, shake vigorously and incubate at room temperature, 15 minutes.
3. Centrifuge at 2K rpm, 10 minutes to remove cell debris.
4. Pour supernatant into a sterile flask, add 500 pI chloroform.
5. Store at 4° C.

Titer Amplified Library

1. Make serial dilutions:
   $10^{-5}$=1 µl amplified phage in 1 ml SM Buffer
   $10^{-6}$=1 µl of the $10^{-3}$ dilution in 1 ml SM Buffer
2. Add 200 µl host (in 10 mM MgSO$_4$) to two tubes
3. Inoculate one with 10 µl $10^{-6}$ dilution ($10^{-5}$).
4. Inoculate the other with 1 µl $10^{-6}$ dilution ($10^{-6}$).
5. Incubate 37° C., 15 minutes.
6. Add about 3 ml 48° C. top agar.
   [50 ml stock containing 150 µl IPTG (0.5M) and 375 µl X-GAL (350 mg/ml)]
7. Plate on 100 mm plates and incubate 37° C., overnight
8. Results:
   gtl 1: 1.7×10$^{11}$/ml
   ZAP® (Stratagene): 2.0×10$^{10}$/ml Example 2

Enzymatic Activity Assay

The following is a representative example of a procedure for screening an expression library prepared in accordance with Example 1. In the following, the chemical characteristic Tiers are as follows:

Tier 1: Hydrolase
Tier 2: Amide, Ester and Acetal
Tier 3: Divisions and subdivisions are based upon the differences between individual substrates which are covalently attached to the functionality of Tier 2 undergoing reaction; as well as substrate specificity.
Tier 4: The two possible enantiomeric products which the protein, e.g. enzyme, may produce from a substrate.

Although the following, example is specifically directed to the above mentioned tiers, the general procedures for testing for various chemical characteristics is ,generally applicable to substrates other than those specifically referred to in this Example.

Screening for Tier 1-hydrolase; Tier 2-amide. Plates of the library prepared as described in Example 1 are used to multiply inoculate a single plate containing 200 µl of LB Amp/Meth, glycerol in each well. This step is performed using the High Density Replicating Tool (HDRT) of the Beckman Biomek with a 1% bleach, water, isopropanol, air-dry sterilization cycle between each inoculation. The single plate is grown for 2 h at 37° C. and is then used to inoculate two white 96-well Dynatech microtiter daughter plates containing 250 µl of LB Arnp/Meth, golycerol in each well. The original single plate is incubated at 37° C. for 18 h, then stored at 80° C. The two condensed daughter plates are incubated at 37° C. also for 18 h. The condensed daughter plates are then heated at 70° C. for 45 min. to kill the cells and inactivate the host *E. coli* proteins, e.g enzymes. A stock solution of 5 mg/mL morphourea phenylalanyl-7-amino4-trifluoromethyl cournarin (MuPheAFC, the 'substrate') in DMSO is diluted to 600 μM with 50 MM pH 7.5 Hepes buffer containing 0.6 mg/mL of the detergent dodecyl maltoside.

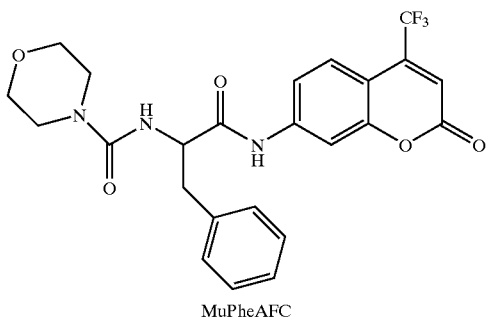

MuPheAFC

Fifty μL of the 600 μM MuPheAFC solution is added to each of the wells of the white condensed plates with one 100 μL mix cycle using the Biomek to yield a final concentration of substrate of ~100 μM. The fluorescence values are recorded (excitation=400 nm, emission=505 nm) on a plate reading fluorometer immediately after addition of the substrate (t=O). The plate is incubated at 70° C. for 100 min, then allowed to cool to ambient temperature for 15 additional minutes. The fluorescence values are recorded again (t=100). The values at t=0 are subtracted from the values at t=100 to determine if an active clone is present.

The data will indicate whether one of the clones in a particular well is hydrolyzing the substrate. In order to determine the individual clone which carries the activity, the source library plates are thaw ed and the individual clones are used to singly inoculate a new plate containing LB Amp/Meth, glycerol. As above, the plate is incubated at 37° C. to grow the cells, heated at 70° C. to inactivate the host proteins, e.g enzymes, and 50 μL of 600 μM MuPheAFC is added using the Biomek. Additionally three other substrates are tested. They are methyl umbelliferone heptanoate, the CBZ-arginine rhodamine derivative, and fluorescein-conjugated casein (~3.2 mol fluorescein per mol of casein).

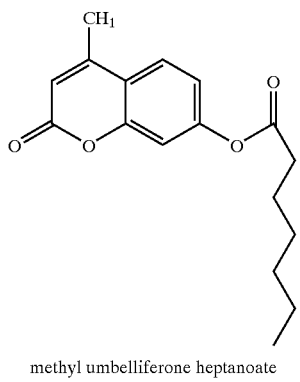

methyl umbelliferone heptanoate

-continued

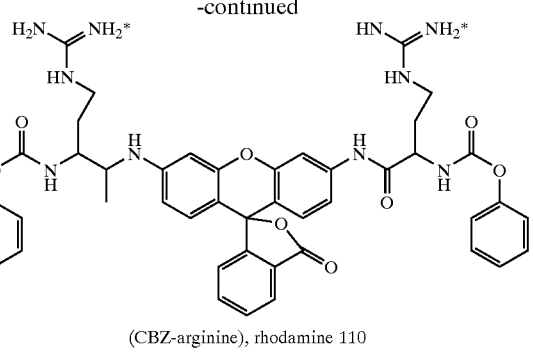

(CBZ-arginine), rhodamine 110

The umbelliferone and rhodamine are added as 600 μM stock solutions in 50 μL of Hepes buffer. The fluorescein conjugated casein is also added in 50 μL at a stock concentration of 20 and 200 mg/mL. After addition of the substrates the t=0 fluorescence values are recorded, the plate is incubated at 70° C., and the t=100 min. values are recorded as above.

These data indicate which plate the active clone is in, where the arginine rhodamine derivative is also turned over by this activity, but the lipase substrate. methyl umbelliferone heptanoate, and protein, fluorescein-conjugated casein, do not function as substrates, the Tier I classification is 'hydrolase' and the Tier 2 classification is amide bond. No cross reactivity should be seen with the Tier 2-ester classification.

As shown in FIG. 1, a recombinant clone from the library which has been characterized in Tier 1 as hydrolase and in Tier 2 as amide may then be tested in Tier 3 for various specificities. In FIG. 1, the various classes of Tier 3 are followed by a parenthetical code which identifies the substrates of Table 1 which are used in identifying such specificities of Tier 3.

Figure 2:
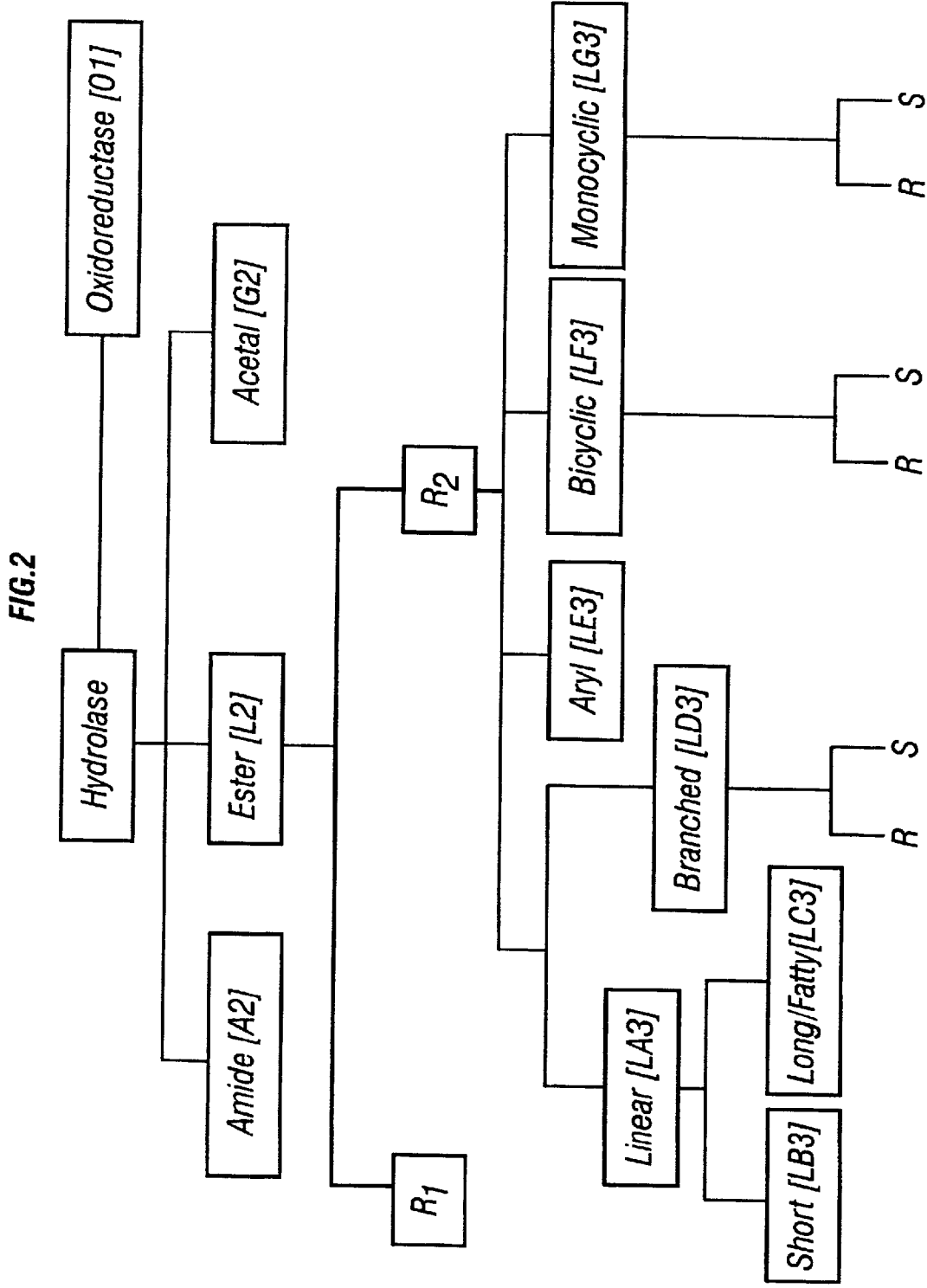
FIG. 2 shows an illustration of a recombinant clone from the library which has been characterized in Tier 1 as hydrolase and in Tier 2 as ester may then be tested in Tier 3 for various specificities.
Figure 3:
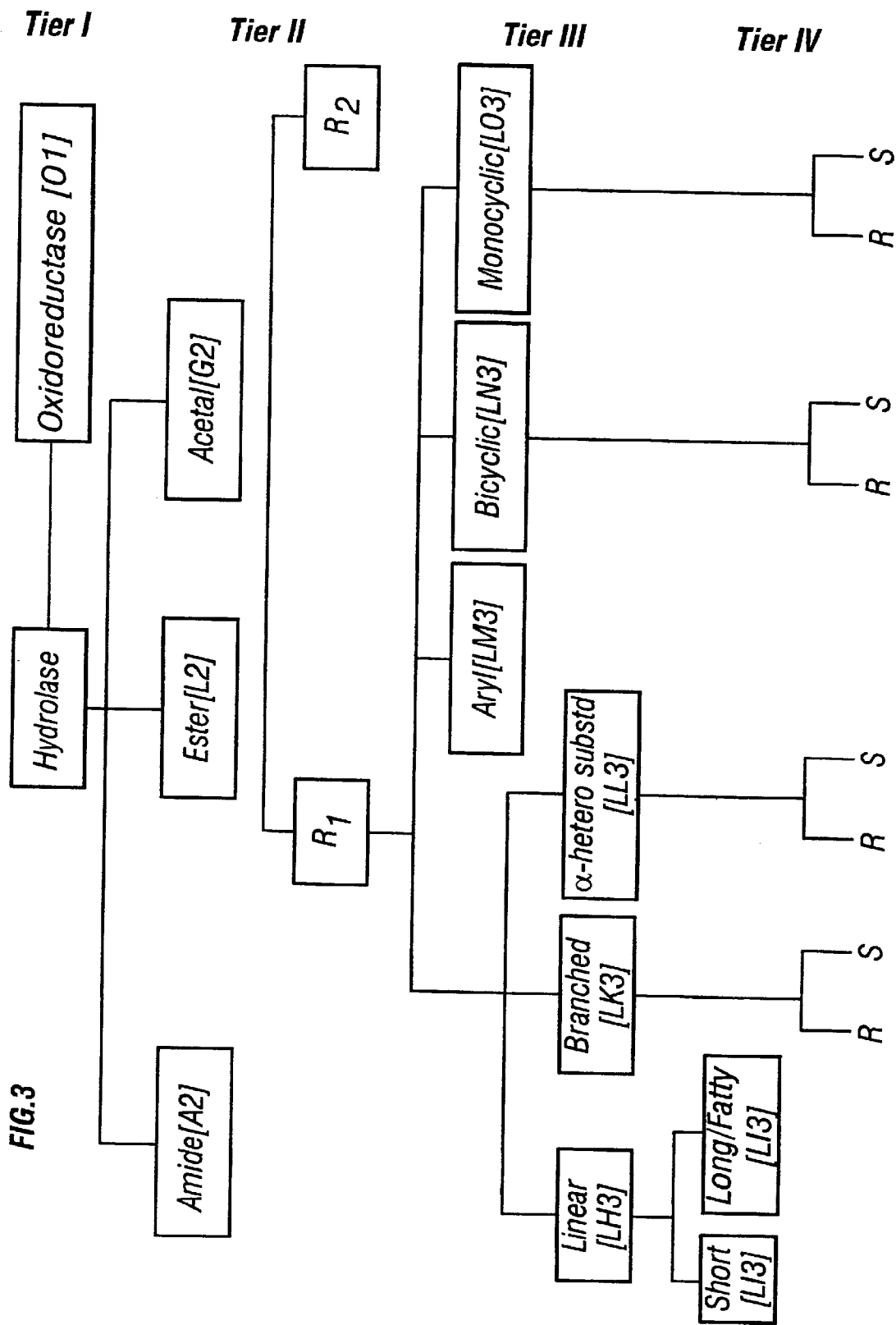

As shown in FIGS. 2 and 3, a recombinant clone from the library which has been characterized in Tier 1 as hydrolase and in Tier 2 as ester may then be tested in Tier 3 for various specificities. In FIGS. 2 and 3, the various classes of Tier 3 are followed by a parenthetical code which identifies the substrates of Tables 3 and 4 which are used in identifying such specificities of Tier 3. In FIGS. 2 and 3, R2 represents the alcohol portion of the ester and R' represents the acid portion of the ester.

Figure 4:
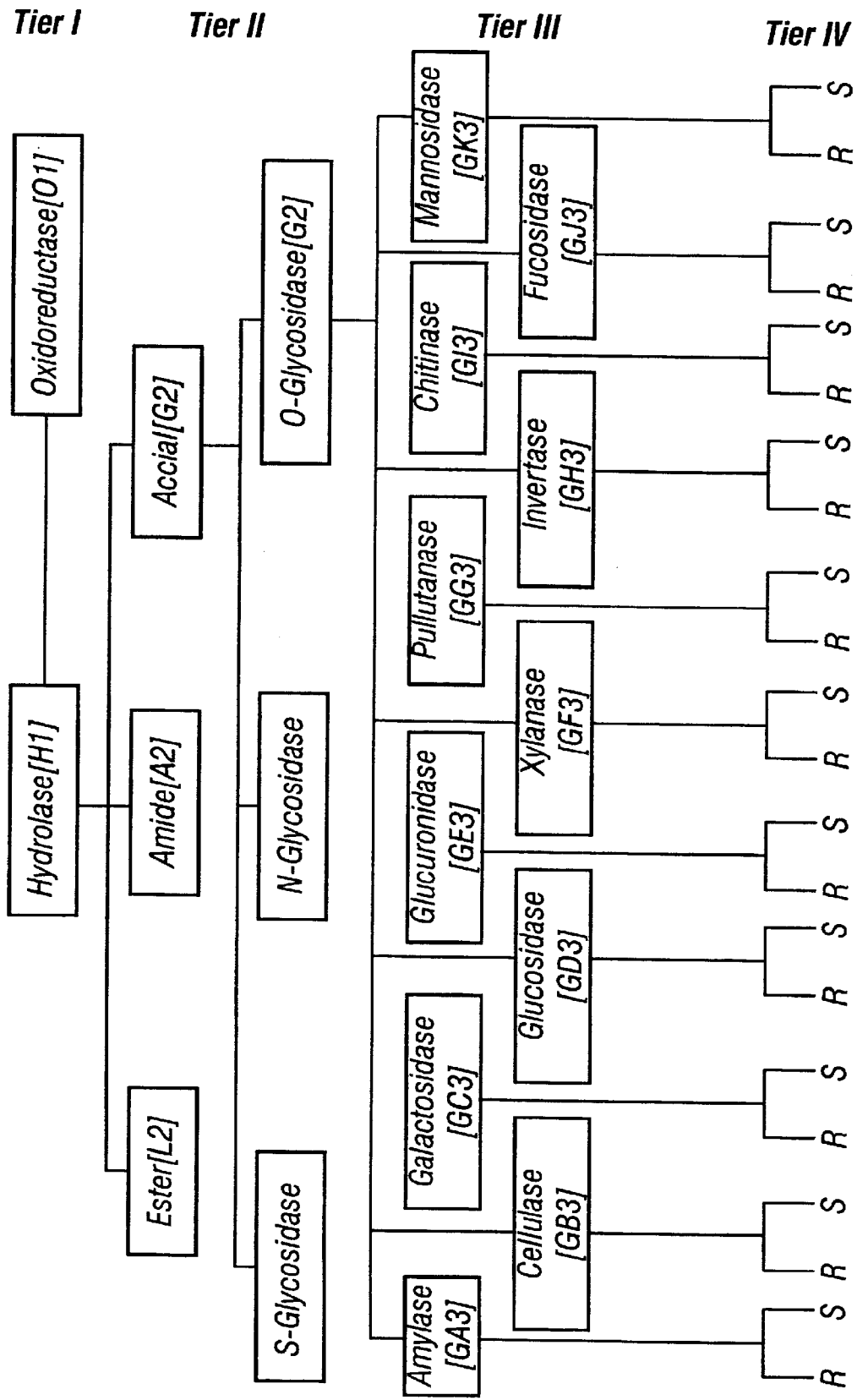
FIG. 4 shows a recombinant clone from the library which has been characterized in Tier 1 as hydrolase and in Tier 2 as acetal may then be tested in Tier 3 for various specificities.

As shown in FIG. 4, a recombinant clone from the library which has been characterized in Tier 1 as hydrolase and in Tier 2 as acetal may then be tested in Tier 3 for various specificities. In FIG. 3, the various classes of Tier 3 are followed by a parenthetical code which identifies the substrates of Table 5 which are used in identifying such specificities of Tier 3.

Proteins, e.g enzymes, may be classified in Tier 4 for the chirality of the product(s) produced by the enzyme. For example, chiral amino esters may be determined using at least the following substrates:

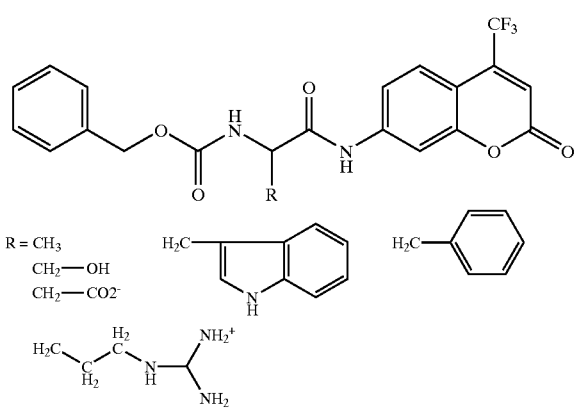

For each substrate which is turned over the enantioselectivity value, E, is determined according to the equation below:

$$E = \frac{\ln[(1 - c(1 + ee_p)]}{\ln[(1 - c(1 - ee_p)]}$$

where $ee_p$=the enantiomeric excess (ee) of the hydrolyzed product and c=the percent conversion of the reaction. See Wong and Whitesides, Proteins, e.g. enzymes, in Synthetic Organic Chemistry, 1994, Elsevier, Tarrytown, N.Y., pp. 9–12.

The enantiomeric excess is determined by either chiral high performance liquid chromatography (HPLC) or chiral capillary electrophoresis (CE). Assays are performed as follows: two hundred pL of the appropriate buffer is added to each well of a 96-well white microtiter plate, followed by 50 μL of partially or completely purified protein, e.g enzyme, solution; 50 μL of substrate is added and the increase in fluorescence monitored versus time until 50% of the substrate is consumed or the reaction stops, whichever comes first.

Example 3

Construction of a Stable, Large Insert Picoplankton Genomic DNA Library

Figure 5:
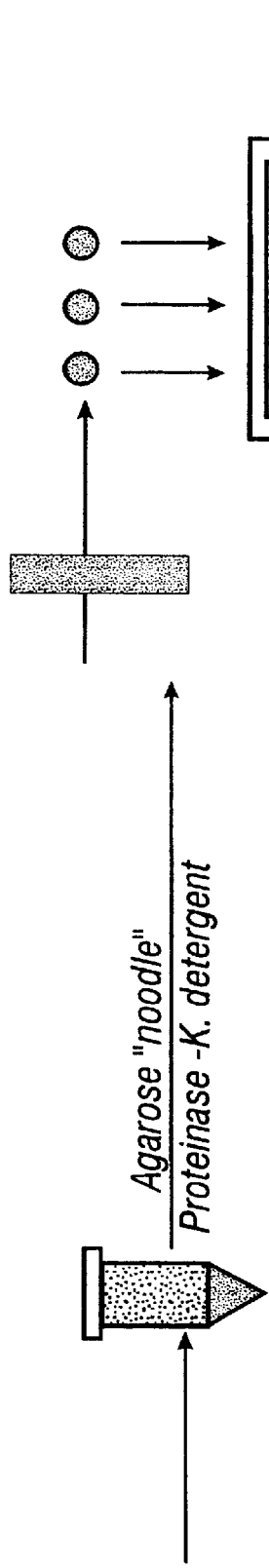
FIG. 5 shows an overview of the procedures used to construct an environmental library from a mixed picoplankton sample.
Figure 5:
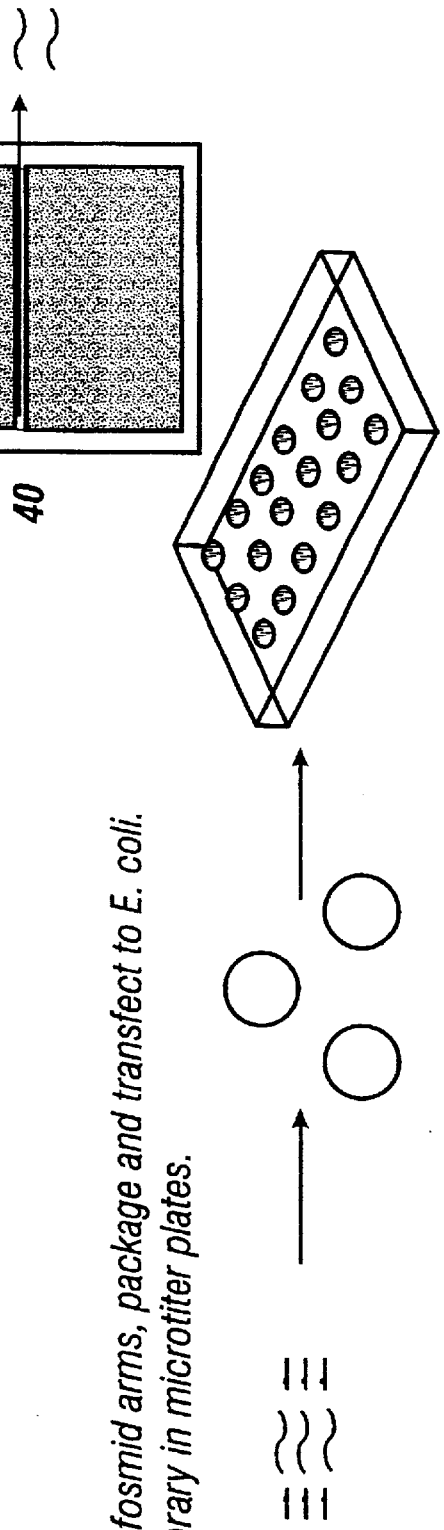

FIG. 5 shows an overview of the procedures used to construct an environmental library from a mixed picoplankton sample. A stable, large insert DNA library representing picoplankton genomic DNA was prepared as follows.

Cell collection and preparation of DNA. Agarose plugs containing concentrated picoplankton cells were prepared from samples collected on an oceanographic cruise from Newport, Oregon to Honolulu, Hawaii. Seawater (30 liters) was collected in Niskin bottles, screened through 10 μm Nitex, and concentrated by hollow fiber filtration (Amicon DC10) through 30,000 MW cutoff polyfulfone filters. The concentrated bacterioplankton cells were collected on a 0.22 1 lm, 47 mm Durapore filter, and resuspended in 1 ml of 2×STE buffer (1M NaCI, 0.1M EDTA, 10 mM Tris, pH 8.0) to a final density of approximately $1 \times 10^{10}$ cells per ml. The cell suspension was mixed with one volume of 1% molten Seaplaque LMP agarose (FMC) cooled to 40° C., and then immediately drawn into a 1 ml syringe. The syringe was sealed with parafilm and placed on ice for 10 min. The cell-containing agarose plug was extruded into 10 ml of Lysis Buffer (10 mM Tris pH 8.0, 50 mM NaCI, 0.1M EDTA, 1% Sarkosyl, 0.2% sodium deoxycholate, 1 mg/ml Iysozyme) and incubated at 37° C. for one hour. The agarose plug was then transferred to 40 mls of ESP Buffer (1% Sarkosyl, 1 mg/ml proteinase K, in 0.5M EDTA), and incubated at 55° C. for 16 hours. The solution was decanted and replaced with fresh ESP Buffer, and incubated at 55° C. for an additional hour. The agarose plugs were then placed in 50 mM EDTA and stored at 4° C. shipboard for the duration of the oceanographic cruise.

One slice of an agarose plug (72 μl) prepared from a sample collected off the Oregon coast was dialyzed overnight at 4° C. against I mL of buffer A (100 mM NaCI, 10 mM Bis Tris Propane-HCI, 100 μg/ml acetylated BSA: pH 7.0 (@25° C.) in a 2 mL microcentrifuge tube. The solution was replaced with 250 μl of fresh buffer A containing 10 mM $MgCl_2$ and 1 mM DTT and incubated on a rocking slatform for 1 hr at room temperature. The solution was then changed to 250 μl of the same buffer containing 4 U of Sau3A1 (NEB), equilibrated to 37° C. in a water bath, and then incubated on a rocking platform in a 37° C. incubator for 45 min. The plug was transferred to a 1.5 ml microcentrifuge tube and incubated at 68° C. for 30 min to inactivate the protein, e.g. enzyme, and to melt the agarose. The agarose was digested and the DNA dephosphorylased using Gelase and HK-phosphatase (Epicentre), respectively, according to the manufacturer's recommendations. Protein was removed by gentle phenol/chloroform extraction and the DNA was ethanol precipitated, pelleted, and then washed with 70% ethanol. This partially digested DNA was resuspended in sterile $H_2O$ to a concentration of 2.5 μg/μl for ligation to the pFOS1 vector.

PCR amplification results from several of the agarose plugs (data not shown) indicated the presence of significant amounts of archaeal DNA. Quantitative hybridization experiments using rRNA extracted from one sample, collected at 200 m of depth off the Oregon Coast, indicated that planktonic archaea in (this assemblage comprised approximately 4.7% of the total picoplankton biomass (this sample corresponds to "PACI"-200 m in Table 1 of DeLong et al., high abundance of Archaea in Antarctic marine picoplankton, Nature, 371:695–698, 1994). Results from archaeal-biased rDNA PCR amplification performed on agarose plug Iysates confirmed the presence of relatively large amounts of archaeal DNA in this sample. Agarose plugs prepared from this picoplankton sample were chosen for subsequent fosmid library preparation. Each 1 ml agarose plug from this site contained approximately 7.5 ×$10^5$ cells, therefore approximately 5.4×$10^5$ cells were present in the 72 μl slice used in the preparation of the partially digested DNA.

Vector arms were prepared from pFOSI as described (Kim et al., Stable propagation of casmid sized human DNA inserts in an F factor based vector, Nucl. Acids Res., 20:10832–10835, 1992). Briefly, the plasmid was completely digested with AstII, dephosphorylated with HK phosphatase, and then digested with BamHI to generate two anns, each of which contained a cos site in the proper orientation for cloning and packaging ligated DNA between 35–45 kbp. The partially digested picoplankton DNA, isolated by partial fragment gel electrophoresis (PFGE), was ligated overnight to the PFOSI arms in a 15 μl ligation reaction containing 25 ng each of vector and insert and 1 U of T4 DNA ligase (Boehringer-Mannheim). The ligated DNA in four microliters of this reaction was in vitro packaged using the Gigapack XL packaging system (Stratagene), the fosmid particles transfected to *E. coli* strain DH10B (BRL), and the cells spread onto $LB_{cm15}$ plates. The resultant fosmid clones were picked into 96-well microliter dishes containing $LB_{cm15}$ supplemented with 7% glycerol. Recombinant fosmids, each containing cat 40 kb of picoplankton DNA insert, yielded a library of 3,552 fosmid clones, containing approximately $1.4 \times 10^8$ base pairs of cloned DNA. All of the clones examined contained inserts ranging from 38 to 42 kbp. This library was stored frozen at −80° C. for later analysis.

Numerous modifications and variations of the present invention are possible in light of the above teachings; therefore, within the scope of the claims, the invention may be practiced other than as particularly described.

TABLE 1

A2

Fluorescein conjugated casein (3.2 mol fluorescein/mol casein)
CBZ-Ala-AMC
t-BOC-Ala-Ala-Asp-AMC
succinyl-Ala-Gly-Leu-AMC
CBZ-Arg-AMC
CBZ-Met-AMC
morphourea-Phe-AMC
t-BOC = t-butoxy carbonyl, CBZ = carbonyl benzyloxy.
AMC = 7-amino-4-methyl coumarin

AA3

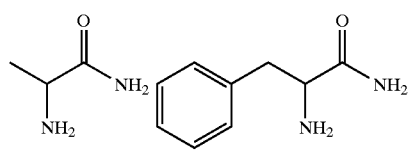

AB3

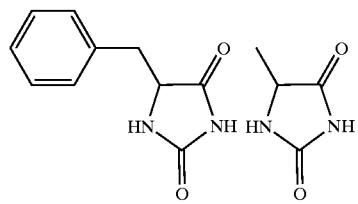

TABLE 1-continued

AC3

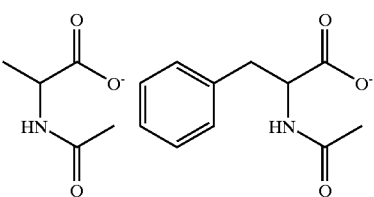

AD3

Fluorescein conjugated casein
t-BOC-Ala-Ala-Asp-AFC
CBZ-Ala-Ala-Lys-AFC
succinyl-Ala-Ala-Phe-AFC
succinyl-Ala-Gly-Leu-AFC
AFC = 7-amino-4-trifluoromethyl coumarin.)

AE3

Fluorescein conjugated casein

AF3 t-BOC-Ala-Ala-Asp-AFC
CBZ-Asp-AFC

AG3

CBZ-Ala-Ala-Lys-AFC
CBZ-Arg-AFC

AH3 succinyl-Ala-Ala-Phe-AFC
CBZ-Phe-AFC
CBZ-Trp-AFC

AI3 succinyl-Ala-Gly-Leu-AFC
CBZ-Ala-AFC
CBZ-Sewr-AFC

TABLE 2

L2

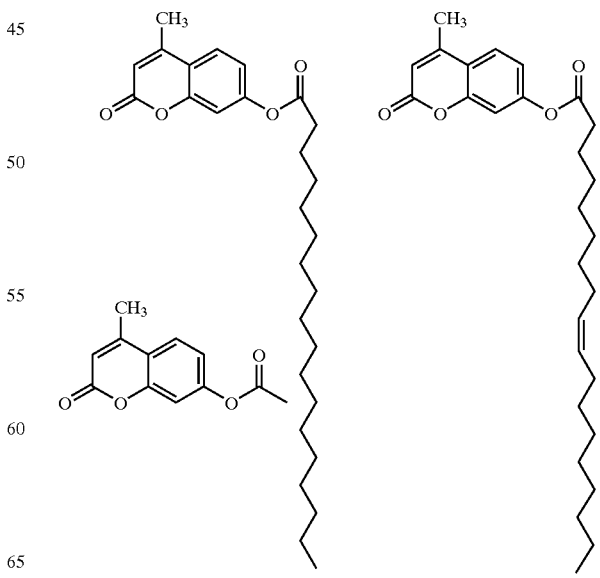

TABLE 2-continued
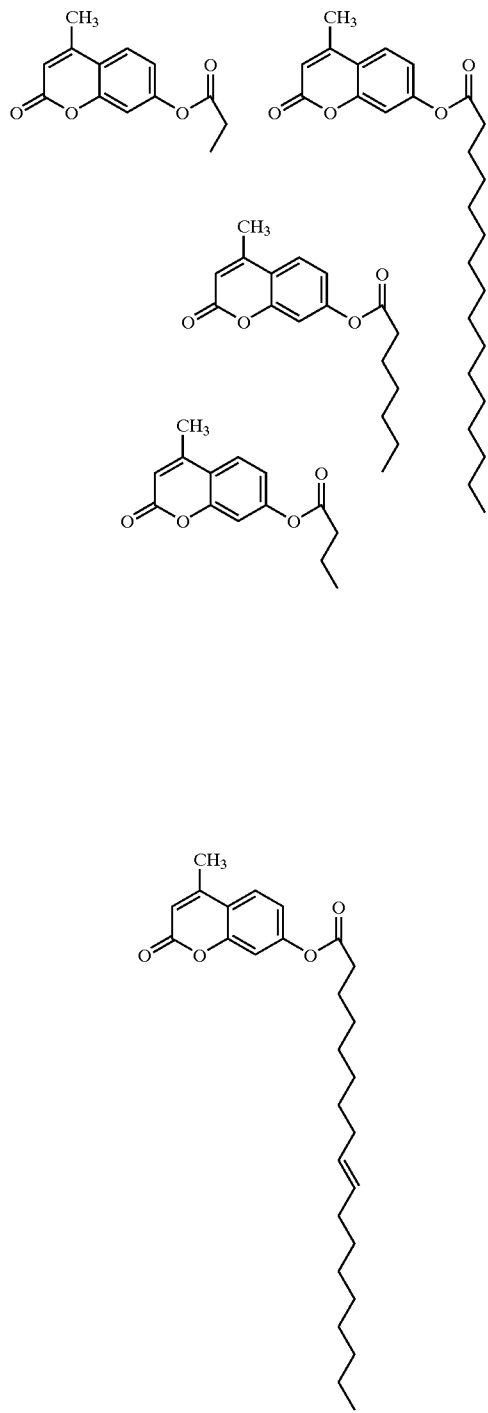
TABLE 2-continued
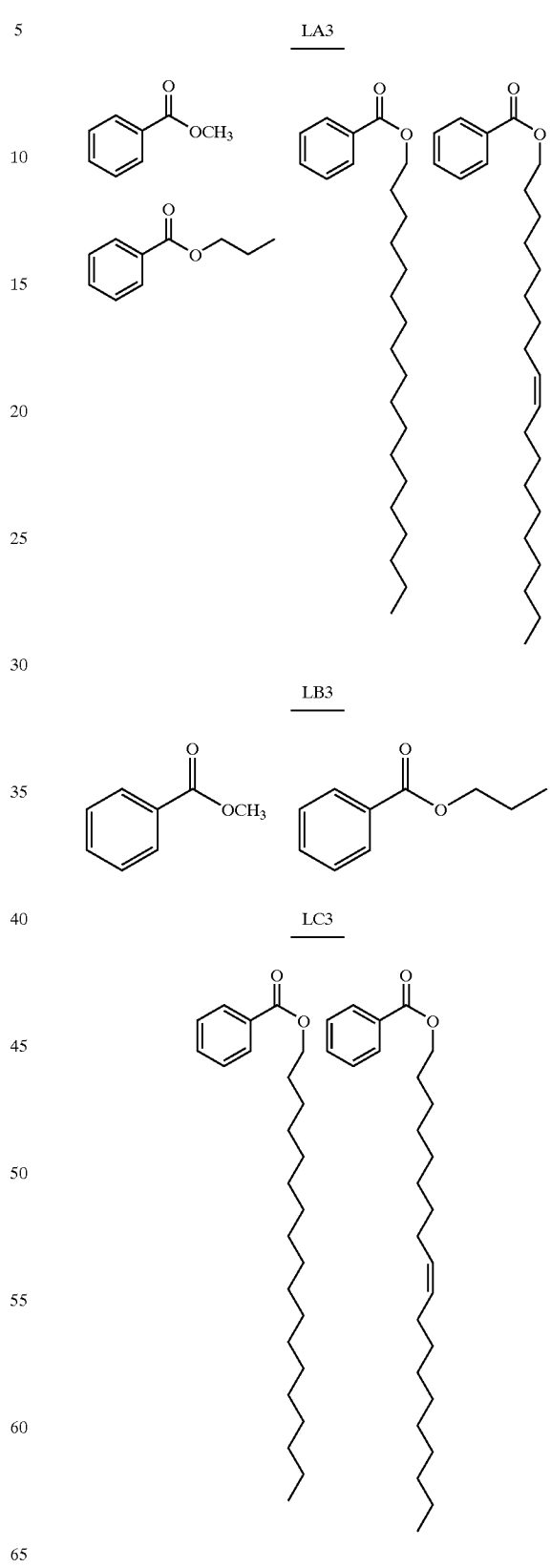

TABLE 2-continued
LD3
LE3
And all of L2
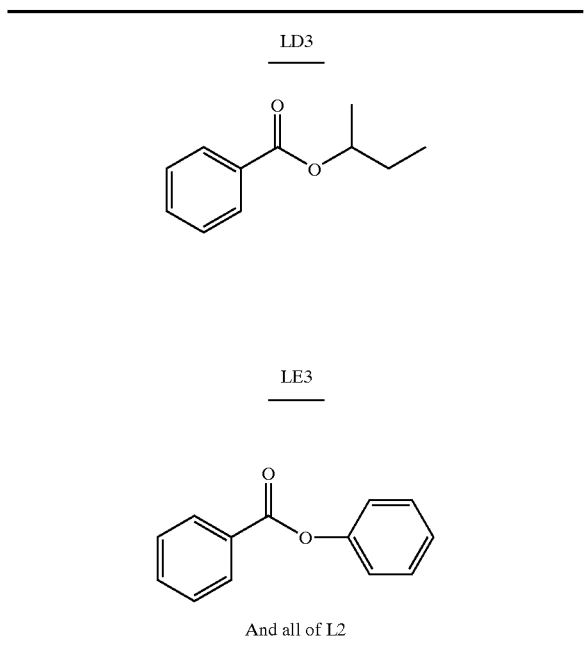
LF3
LG3
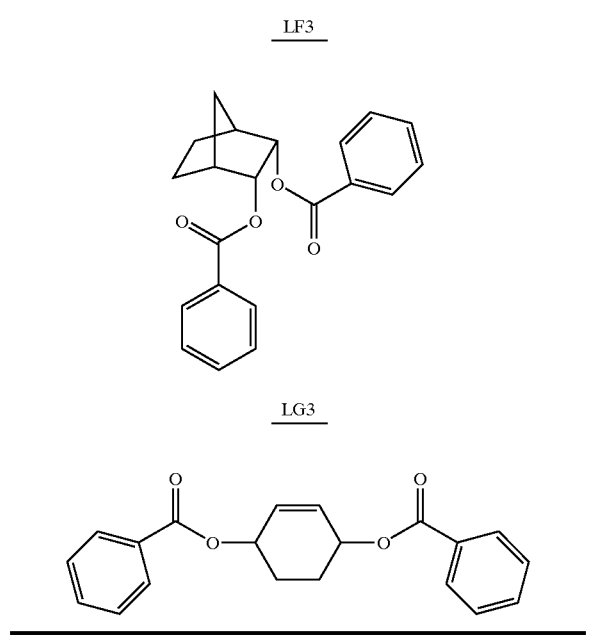
TABLE 3
LH3
And all of L2
LI3
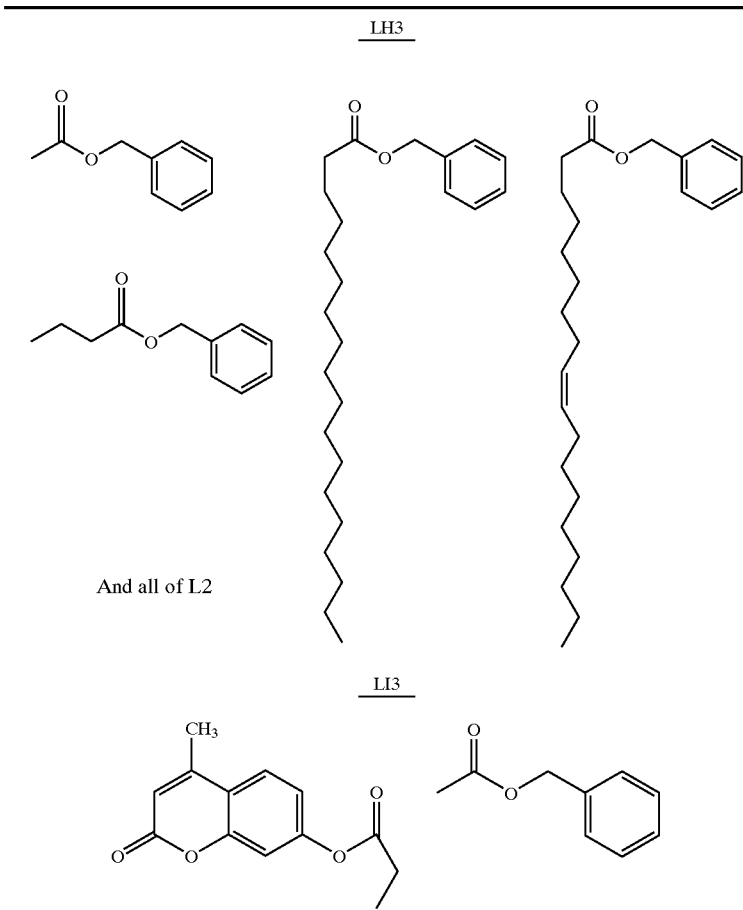

TABLE 3-continued
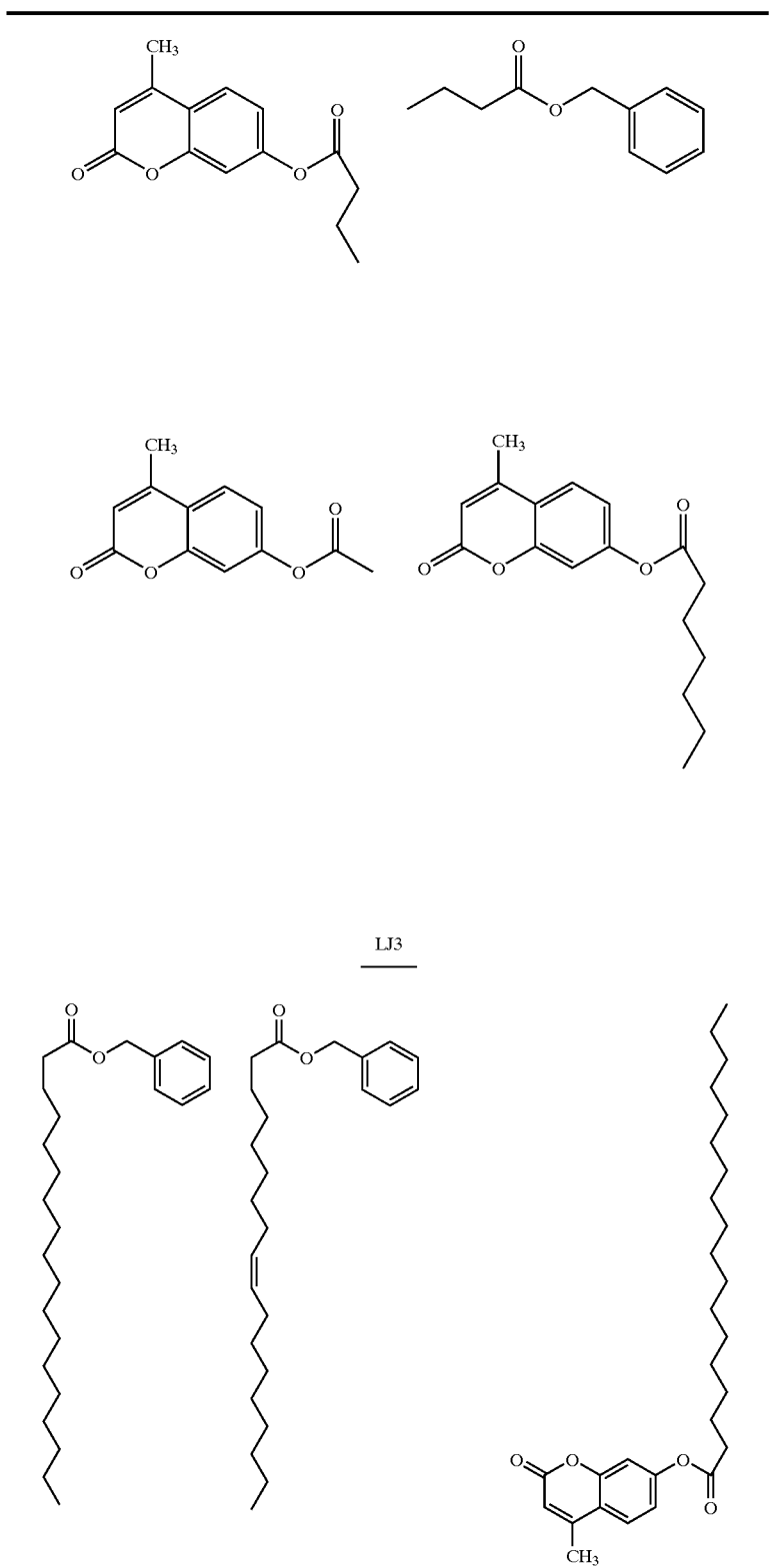
LJ3

TABLE 3-continued
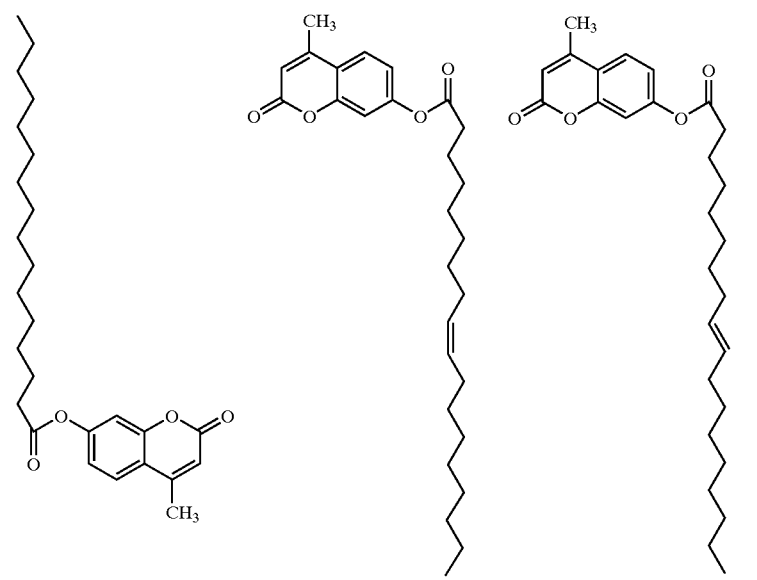
LK3
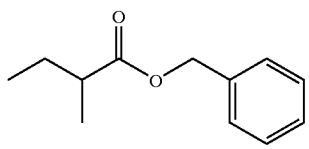
LL3
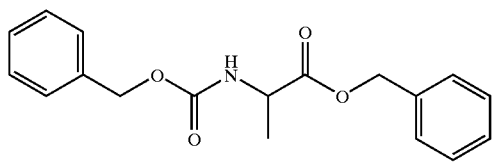
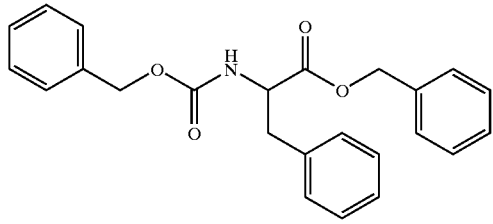
LM3
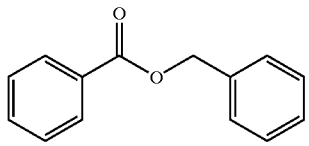

TABLE 3-continued

LN3

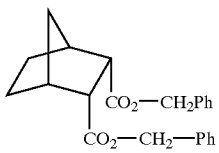

LO3

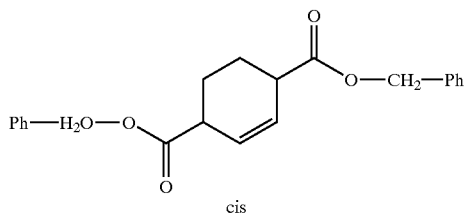

cis

TABLE 4

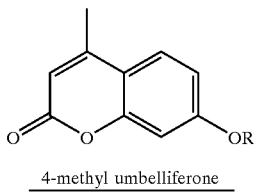

4-methyl umbelliferone

| wherein R = | |
|---|---|
| G2 | β-D-galactose |
| | β-D-glucose |
| | β-D-glucuronide |
| GB3 | β-D-cellotrioside |
| | β-D-cellobiopyranoside |
| GC3 | β-D-galactose |
| | α-D-galactose |
| GD3 | β-D-glucose |
| | α-D-glucose |
| GE3 | β-D-glucoronide |
| GI3 | β-D-N,N-diacetylchitobiose |
| GJ3 | β-D-fucose |
| | α-L-fucose |
| | β-L-fucose |
| GK3 | β-D-mannose |
| | α-D-mannose |
| | non-Umbelliferyl substrates |
| GA3 | amylose [polyglucan α1,4 linkages], amylopectin [polyglucan branching α1,6 linkages] |
| GF3 | xylan [poly, 1,4-D-xylan] |
| GG3 | amylopectin, pullulan |
| GH3 | sucrose, fructofuranoside |

What is claimed is:

1. A method for identifying a protein activity of interest comprising:
   culturing a gene expression library comprising a pool of expression constructs, each expression construct comprising a vector containing one or more cDNA or genomic DNA fragments, wherein the cDNA or genomic DNA fragments in the pool of expression constructs are derived from a plurality of species of donor eukaryotic organisms, and wherein the cDNA or genomic DNA fragments are each operably-associated with one or more regulatory regions that drives expression of genes encoded by the cDNA or genomic DNA fragments in an appropriate host organism; and
   detecting the protein activity encoded by the cDNA or genomic DNA fragments.

2. The method of claim 1, wherein the protein activity is enzymatic activity.

3. The method of claim 2, wherein the enzymatic activity is selected from the group consisting of oxidoreductase, transferase, hydrolase, lyase, isomerase, and ligase activity.

4. The method of claim 1, wherein the donor eukaryotic organisms are microorganisms.

5. The method of claim 4, wherein the microorganisms are derived from an environmental sample.

6. The method of claim 4, wherein the microorganisms are a mixed population of uncultured organisms.

7. The method of claim 1, wherein the DNA fragment comprises one or more operons, or portions thereof.

8. The method of claim 7, wherein the operon or portions thereof encodes a complete or partial metabolic pathway.

9. The method of claim 1, wherein the organisms are fungi.

10. The method of claim 1, wherein the organisms are algae.

11. The method of claim 1, wherein the organisms are protozoan.

12. The method of claim 5, wherein the organisms are extremophiles.

13. The method of claim 12, wherein the organisms are thermophiles, hyperthermophiles, psychrophiles, or psychrotrophs.

14. The method of claim 1, wherein the host organism is a bacterial cell.

15. The method of claim 14, wherein the bacterial cell is an *E. coli*, Bacillus, Streptomyces, or *Salmonella typhimurium* cell.

16. The method of claim 1, wherein the host organism is a fungal cell.

17. The method of claim 16, wherein the fungal cell is a yeast cell.

18. The method of claim 1, wherein the host cell is a Drosophila S2 or a Spodoptera S9 cell.

19. The method of claim 1, wherein the host organism is an animal cell.

20. The method of claim 19, wherein the animal cell is a CHO, COS or *Bowes melanoma* cell.

21. The method of claim 1, wherein the host organism is a plant cell.

22. A method for identifying a protein activity of interest comprising:

culturing a gene expression library comprising a pool of expression constructs, each expression construct comprising a vector containing one or more cDNA or genomic DNA fragments, wherein the cDNA or :genomic DNA fragments in the pool of expression constructs are derived from a plurality of species of donor organisms, and wherein the cDNA or genomic DNA fragments are each operably-associated with one or more regulatory regions that drives expression of genes encoded by the cDNA or genomic DNA fragments in an appropriate host organism, wherein the host organism is a bacterial cell; and detecting the protein activity encoded by the cDNA or genomic DNA fragments.

23. A method for identifying a protein activity of interest comprising:

culturing a gene expression library comprising a pool of expression constructs, each expression construct comprising a vector containing one or more cDNA or genomic DNA fragments, wherein the cDNA or genomic DNA fragments in the pool of expression constructs are derived from a plurality of species of donor organisms, and wherein the cDNA or genomic DNA fragments are each operably-associated with one or more regulatory regions that drives expression of genes encoded by the cDNA or genomic DNA fragments in an appropriate host organism, wherein the host organism is a fungal cell; and detecting the protein activity encoded by the cDNA or genomic DNA fragments.

24. A method for identifying a protein activity of interest comprising:

culturing a gene expression library comprising a pool of expression constructs, each expression construct comprising a vector containing one or more cDNA or genomic DNA fragments, wherein the cDNA or genomic DNA fragments in the pool of expression constructs are derived from a plurality of species of donor organisms, and wherein the cDNA or genomic DNA fragments are each operably-associated with one or more regulatory regions that drives expression of genes encoded by the cDNA or genomic DNA fragments in an appropriate host organism, wherein the host organism is a plant cell; and detecting the protein activity encoded by the cDNA or genomic DNA fragments.

25. A method for identifying a protein activity of interest comprising:

culturing a gene expression library comprising a pool of expression constructs, each expression construct comprising a vector containing one or more cDNA or genomic DNA fragments, wherein the cDNA or genomic DNA fragments in the pool of expression constructs are derived from a plurality of species of donor organisms, and wherein the cDNA or genomic DNA fragments are each operably-associated with one or more regulatory regions that drives expression of genes encoded by the cDNA or genomic DNA fragments in an appropriate host organism, wherein the host organism is an animal cell; and detecting the protein activity encoded by the cDNA or genomic DNA fragments.

* * * * *